United States Patent [19]

Henry

[11] Patent Number: 4,625,573

[45] Date of Patent: Dec. 2, 1986

[54] MAGNETIC SHIELDING AND MAGNETICALLY SHIELDED BOREHOLE CORE DRILLING

[75] Inventor: William E. Henry, Bartlesville, Okla.

[73] Assignee: Phillips Petroleum Company, Bartlesville, Okla.

[21] Appl. No.: 737,372

[22] Filed: May 23, 1985

[51] Int. Cl.$^4$ .............................................. G01N 1/08
[52] U.S. Cl. ............................. 73/864.44; 324/377; 73/864.45
[58] Field of Search ........................ 73/864.44, 864.45; 324/376, 377; 336/84 R, 84 M; 408/204; 361/424; 175/226; 166/65.1; 174/35 R

[56] References Cited

U.S. PATENT DOCUMENTS

| | | | |
|---|---|---|---|
| 1,709,054 | 4/1929 | Bennet | 336/84 M |
| 2,260,562 | 10/1941 | Dillon | 175/182 |
| 2,487,547 | 11/1949 | Harvey | 174/35 R |
| 3,534,311 | 10/1970 | Bell | 336/84 |
| 3,617,868 | 11/1971 | Beltel | 324/13 |
| 3,820,012 | 6/1974 | Molyneux | 324/14 |
| 4,211,974 | 7/1980 | Henry | 324/377 |
| 4,340,770 | 7/1982 | Bridges et al. | 174/35 |

OTHER PUBLICATIONS

Combining Netic Alloy Magnetic Shielding and Convection Cooling-Magnetic Shield Division, Perfection Mica Company, Apr. 8, 1959.
McGraw-Hill Encyclopedia, McGraw Hill Book Company, vol. 8, Table 1, pp. 34-36; vol. 10, pp. 22-23; vol. 5, pp. 229-234.
Bozorth, Richard M., "Ferromagnetism" pp. 5-7, D. Van Nostrand Co., Inc.

Primary Examiner—Stephen A. Kreitman
Assistant Examiner—Scott M. Oldham
Attorney, Agent, or Firm—William R. Sharp

[57] ABSTRACT

A magnetic shielding member is provided, according to one aspect of the invention, which can be used to effectively shield a borehole core from ambient magnetic fields during drilling of a core specimen from the borehole core. The shielding member comprises a first portion and a second portion, wherein the first portion is hollow and has a first opening in a wall thereof, and wherein the second portion is hollow and includes a sidewall which extends outwardly from the exterior surface of the first portion so as to surround the first opening. The second portion sidewall extends to an open end which defines a second opening. Each portion is constructed of a high permeability ferromagnetic material having permeability characteristics herein defined. In use, a borehole core is positioned in the chamber defined within the first portion, and a drill bit is inserted through the first and second openings so as to extend into the chamber and come into cutting contact with the borehole core. According to other aspects, an apparatus and method are provided, wherein a borehole core is positioned within a hollow magnetic shielding member constructed of a material as defined above. A drill bit is inserted through an opening in the shielding member so as to come into cutting contact with the core.

27 Claims, 3 Drawing Figures

MAGNETIC SHIELDING AND MAGNETICALLY SHIELDED BOREHOLE CORE DRILLING

BACKGROUND OF THE INVENTION

In one aspect, the invention relates to a magnetic shielding member. According to another aspect, this invention relates to a magnetically shielded drilling apparatus. According to yet another aspect of the invention, the invention relates to a method of drilling core specimens from a borehole core wherein the borehole core is effectively shielded from ambient magnetic fields.

During the drilling of a borehole in the search for oil or other minerals, borehole core samples are typically cut from the formations being traversed and are removed to the earth's surface for examination. Various valuable information can be obtained from such borehole cores via magnetic analysis, such as by paleomagnetic analysis wherein the natural remanent magnetism in the borehole core is detected. Natural remanent magnetism is that magnetism which was imparted to the rock by the earth's magnetic field as the rock formed. Probably the most important information obtainable by magnetic analysis of borehole cores is the dip and strike of fractures and of bedding planes in the core. Such information is determined by first determining the direction of the natural remanent magnetism in the borehole core by paleomagnetic analysis. From the magnetic direction, the original orientation of the borehole core in the earth can be determined. Once the original orientation is known, the correct strike and dip of fractures and of bedding planes in the core can be determined by observing such planes. Alternatively, other magnetic analysis techniques could be employed, such as those wherein a magnetic field is imposed artificially on the core before its removal from the surrounding subterranean formation.

It is known that borehole core samples are sensitive to ambient fields, such as the earth's, and can thus take on magnetic overprints resulting from exposure to such ambient fields. Obviously, such overprints can interfere in magnetic analysis of the core. Thus, magnetic analysis of borehole cores is frequently done in a magnetically shielded environment.

Magnetic overprinting from ambient fields has also been found to be a problem during drilling of a borehole core before a magnetic analysis procedure. Typically, small core specimens are drilled from the borehole core, such specimens being subsequently analyzed as discussed above. According to one prior method which attempts to compensate for possible magnetic overprinting during drilling, two core specimens on opposite sides of the borehole core are drilled therefrom. Such core specimens are sometimes referred to as antiparallel specimens. Overprinting in the antiparallel specimens can be cancelled out during magnetic analysis. It should be noted however, that according to such a technique two core specimens are required for an effective analysis, resulting in increased analysis time and cost.

SUMMARY OF THE INVENTION

It is, therefore, an object of the invention to provide an apparatus and method of drilling core specimens from a borehole core which enables drilling of only one core specimen which can be effectively analyzed without substantial harmful effects from overprinting.

It is also an object of the invention to provide an apparatus which can effectively shield a borehole core from ambient fields during drilling so as to avoid overprinting during the drilling operation.

According to one aspect of the invention, a magnetic shielding member is provided which comprises a first portion and a second portion, hereinafter defined, each of which is composed of a ferromagnetic shielding material which is characterized by an initial magnetic permeability of at least about 10,000 gauss/oersted. The first portion is hollow and includes a wall having an opening therethrough. The second portion has a first end at which the second portion meets the first portion at the exterior surface of the first portion. The second portion also has a second open end and a side wall which extends between the ends, wherein the side wall extends outwardly from the exterior surface of the first portion wall so as to generally surround the above mentioned opening. In addition, the opening is in communication with the interior space defined within the second portion sidewall. A magnetic shielding member as described above which contains a borehole core being drilled has been shown to be highly effective in shielding the borehole core so as to prevent magnetic overprinting.

According to another aspect of the invention, an apparatus is provided which includes a shielding member composed of a ferromagnetic material having permeability characteristics as described above, wherein the shielding member has an opening in the wall thereof and has a chamber defined therein. The apparatus further includes a drilling means which includes a drill bit adapted to be received through the opening in the shielding member so as to extend into the chamber.

According to yet another aspect of the invention, a method of drilling a core specimen from a borehole core comprises the steps of: positioning the borehole core in a chamber defined within a hollow shielding member which has an opening in a wall thereof, the member being composed of a ferromagnetic material, and wherein the borehole core is positioned adjacent to the opening; and drilling a core specimen from the borehole core with a drilling means which includes a drill bit, wherein the drill bit is inserted through the opening so as to extend into the chamber and come into cutting contact with the borehole core.

According to a preferred embodiment of the invention described herein, the above described second portion of the shielding member generally tapers toward the axis of the second portion from its first end to its second end. Moreover, the first portion is preferably cylindrical in shape. In operation, a drill bit extends through the second open end of the second portion and the opening in the first portion so as to extend into the chamber defined by the first portion.

A core specimen drilled from a borehole core which has been magnetically shielded according to the invention has been found to have little or no magnetic overprinting from ambient fields. Therefore, there is no need to drill two antiparallel plugs in order to cancel out the magnetic overprints as in the above described prior method. Accordingly, a given magnetic analysis study could be done with half as many samples as are required by the prior method, resulting in significant savings in both cost and time.

DESCRIPTION OF THE PREFERRED EMBODIMENTS

A preferred embodiment of the invention will now be described with reference to the FIGURES. It should be understood that although the embodiment is described in terms of drilling a borehole core, according to certain aspects of the invention the invention could be applied to drilling objects other than a borehole core. According to other aspects of the invention, the magnetic shielding member hereinafter described could be employed to magnetically shield in environments other than in a drilling operation.

Figure 1:
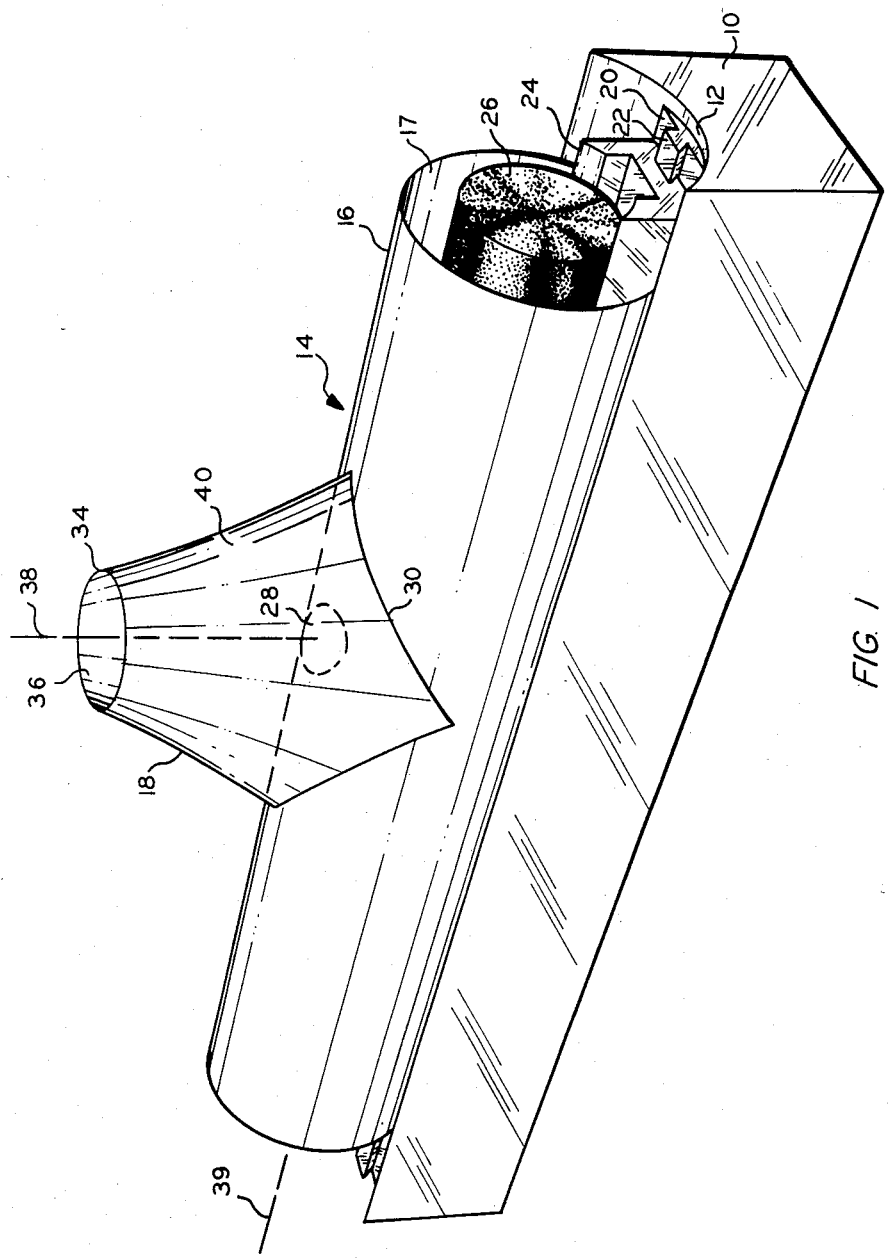
FIG. 1 is a pictorial view of an apparatus according to one embodiment of the invention.

Referring now to FIG. 1, the illustrated apparatus includes a base 10 which is composed of any suitably sturdy nonmagnetic material such as aluminum or brass. As shown, base 10 has a curved upper surface 12.

A hollow magnetic shielding member 14 is provided which comprises a hollow first portion 16, having an interior surface which defines a chamber 17 therein, and a second portion 18 which extends outwardly from the exterior surface of first portion 16. Shielding member 14 will be described in further detail below. As shown, first portion 16 is preferably cylindrical in the illustrated embodiment, and is fixedly mounted by any convenient means to the upper curved surface 12 of base 10.

A track 20 extends longitudinally through chamber 17 so as to be in contact with the interior surface of portion 16, and is fixedly mounted to portion 16 and base 10. Track 20 has an upwardly protruding shoulder 22 which extends along the entire length of the track. A sliding support member 24 is slidably mounted to track 20 by means of a longitudinally extending groove designed to mate with shoulder 22. Support member 24 is adapted to support thereon a borehole core 26, which is most typically cylindrical in shape as shown. Both track 20 and support member 24 are preferably constructed of a nonmagnetic material such as aluminum. Most preferably, the material employed for support 24 is different than the track material to assist in preventing jamming.

A more detailed description of shield member 14 will now be set forth, wherein first portion 16 will first be considered. First portion 16 is composed of a ferromagnetic material. As used herein and in the appended claims, a material is "ferromagnetic" if it has as one of its constituents at least one of iron, cobalt or nickel. According to certain aspects of the invention, the ferromagnetic material employed is characterized by an initial magnetic permeability of at least 10,000 gauss/oersted, most preferably at least about 20,000 gauss/oersted. With respect to the meaning of "initial magnetic permeability", the more general term, "magnetic permeability", will first be defined. "Magnetic permeability" as used herein is "absolute magnetic permeability" $\mu$. $\mu = B/H$, where B is the flux density produced in the material in question by a magnetic field, and where H is the intensity of the field. As known to those skilled in the art, the permeability of ferromagnetic materials is not constant, but is dependent upon the intensity of the magnetic field to which they are exposed. As used herein and in the appended claims, the term "initial magnetic permeability" is defined as the limit approached by the magnetic permeability for a particular material as B and H are decreased toward zero. Employing a ferromagnetic material having initial magnetic permeability characteristics described above provides effective magnetic shielding in the relatively low strength ambient fields to which a borehole core is exposed during drilling. Ambient fields in the environment of core drilling includes not only the earth's magnetic field, but also magnetic fields from parts of the drilling apparatus, such as the drill bit drive shaft, which have become magnetized due to various factors. Such factors include stress and heat encountered during drilling.

With respect to another characteristic of the material, coercivity, it is preferred that the ferromagnetic material has a coercivity of less than about 0.1 oersted, and most preferably less than about 0.06 oersted.

Examples of preferred commercially available metallic alloys having the permeability and coercivity characteristics described above include the following, wherein compositions of the alloys are given in parentheses in terms of weight percent: 4-79 Permalloy (4% Mo, 79% Ni, 17% Fe), Supermalloy (5% Mo, 79% Ni, 16% Fe), 1040 alloy (3% Mo, 14% Cu, 72% Ni, 11% Fe), Sendust (5% Al, 10% Si, 85% Fe) and Mumetal (5% Cu, 2% Cr, 77% Ni, 16% Fe). Reference may be made to the *McGraw-Hill Encyclopedia of Science and Technology*, Volume 8, page 35 for a listing of initial permeabilities and coercivities for these alloys. In addition, the alloys are commercially available from several sources. Mumetal, for example, is available from Allegheny Ludlum Steel Co. of Pittsburgh, Pa. Other commercially available alloys suitable for use with the present invention include: Eagle AAA sheet stock, manufactured by Eagle Magnetic Co., Inc. of Indianapolis, Ind.; Co-netic AA sheet stock, manufactured by Perfection Mica Co., Magnetic Shield Division, of Bensenville, Ill.; and HY-MU-80 sheet stock, manufactured by Ad-vance Magnetics, Inc. of Rochester, Ind. Although not presently preferred, various metallic glasses could also be employed as the ferromagnetic material, such metallic glasses consisting primarily of iron, cobalt, or nickel, and also consisting of a metalloid such as boron or phosphorous and other metallic constituents.

First portion 16 comprises a wall which can have a wide range of thicknesses. It has been found that, generally speaking, results in terms of magnetic shielding generally improve with increasing thickness. By way of example, the thickness of the first portion wall might be in the range of about 0.25 mm to about 1 mm, a thickness within this range achieving a good balance between mechanical strength, material expense and quality of shielding results.

Preferably, first portion 16 is cylindrical in shape for several reasons. First, the magnetic flux of the ambient field will tend to follow a cylindrical smoothly curved wall better than a wall having a shape which requires crimping in its fabrication to produce edges, as in a rectangularly shaped wall. Such crimping affects the crystalline properties of a high permeability metal alloy like one of those noted above. Second, fabrication of a cylindrical wall is cheaper and simpler to fabricate than other shapes requiring crimping. Cylindrical portion 16 can be fabricated by first forming a piece of sheet stock into the desired cylindrical shape, followed by heliarc welding and hydrogen annealing along the lines of joinder between ends of the sheet.

As shown, the wall of portion 16 has an opening 28 therethrough which is in communication with chamber 17, and which is adapted to receive a drill bit therethrough so as to extend into chamber 17. Opening 28 is preferably located approximately at the longitudinal center of portion 16. Such a position for opening 28 ensures that the magnetic shielding effect of portion 16 is at a maximum where drilling takes place in chamber 17 under opening 28. This will become more apparent below.

Each end of portion 16 is open, thus permitting easy and convenient position of borehole core 26 within chamber 17 by means of track 20 and support member 24. Providing open ends on portion 16 does not significantly affect the extent to which magnetic overprinting is prevented by the illustrated apparatus for reasons which follow. Even more importantly, it will also become apparent from the following discussion why the excellent shielding of opening 28 by portion 18, hereinafter described, is significant in the prevention of overprinting in core specimens drilled from the borehole core.

It has been found that the heat and stress associated with drilling makes the borehole core more susceptible to picking up and holding magnetic overprints resulting from exposure to ambient fields. Such overprints picked up by the core where drilling takes place tend to be "hard" and very difficult to remove, as opposed to the "soft" core magnetization in regions of the core away from the drilling region. Thus, one of the primary objectives of the invention is effective shielding of the borehole core at the drilling area, whereas shielding in areas not immediately adjacent to the drilling area is much less of a concern.

In regions of the earth a substantial distance north or south from the equator, such as the United States, the earth's magnetic flux lines are fairly steep with respect to the horizontal. Flux lines from, for example a magnetized drill bit drive shaft above the illustrated apparatus are also generally quite steep. Thus, providing the length to diameter ratio of portion 16 is large enough, flux entering open ends of portion 16 tend to be received by the wall of portion 16 before reaching the midsection of portion 16 where drilling of the borehole core takes place, due to the central position of opening 28. Additionally, portion 16 preferably has sufficient length so that the borehole core at the midsection drilling area is far enough away from ends of portion 16 to avoid edge effects at the ends, where flux tends to be concentrated. In view of the above considerations, the length of portion 16 is preferably several times that its inside diameter, the length most typically being at least about 18 inches.

Thus, if portion 16 is constructed as discussed above and as illustrated, the critical portion of the borehole core which is being drilled is magnetically shielded even though the ends of portion 16 are open.

It should be noted that it may be desirable to provide caps on the ends of portion 16 if used near the equator where flux lines of the earth's magnetic field are nearly horizontal. However, one can effectively shield with open ends near the equator so long as the chamber axis is generally perpendicular to the earth's magnetic field. If the chamber axis is not exactly perpendicular to the earth's field, the incoming flux will be much higher near the equator than it would be at higher latitudes so that operation with caps would be preferable. Also, the length of portion 16 is still important if open ends are used since a longer cylindrical portion can be positioned further from perpendicular to earth's field before its shielding effect at its center is decreased.

Second portion 18 will now be described in greater detail. Second portion 18 is of a ferromagnetic material having permeability characteristics as previously described with reference to portion 16, and also preferably having the above described coercivity characteristics. Moreover, one of the previously mentioned alloys could be used for portion 18. The same material or a different material from that employed for portion 16 could be utilized for portion 18, depending primarily on practical factors and convenience of fabrication. In this regard, it may be more convenient to employ a foil only a fraction of the thickness of the portion 16 material, since such a foil is easy to form into the desired shape. After forming into the desired shape, the high permeability material employed is preferably heliarc welded and hydrogen annealed, although heliarc welding and hydrogen annealing may not be necessary if foil is used.

Second portion 18 has a lower end 30 at which the second portion meets the wall of first portion 16 at the exterior surface thereof. According to the illustrated embodiment, portions 16 and 18 are separate members, wherein portion 18 is mounted to portion 16 such that lower end 30 of portion 18 is in intimate contact, or more specifically good flux contact, with the exterior surface of portion 16. It should be understood, however, that it may be preferable that shielding member 14 be one integral piece, but such a construction would be more difficult to fabricate. Excellent flux contact between lower end 30 and the exterior surface of portion 16 in the illustrated embodiment can be provided by heliarc welding followed by annealing, although any technique for providing good flux contact could be employed. It would not be desirable to connect lower end 30 to portion 16 by means of a low permeability material such as glue, for example.

Portion 18 also has an upper open end 34 generally opposite lower end 30. Open end 34 defines an opening 36 which is aligned with opening 28, and which is adapted to receive a drill bit therethrough, as will become more apparent with reference to FIG. 3. Additionally, portion 18 has an axis 38 which preferably intersects the centers of openings 28 and 36. Axis 38 also is generally perpendicular to the longitudinal axis 39 of portion 16 in the illustrated embodiment, such an arrangement providing effective shielding as well as convenient compatibility with a vertically oriented drill bit.

Portion 18 has a sidewall 40 which extends between ends 30 and 34, and which extends outwardly from the exterior surface of the wall of portion 16 so as to generally surround opening 28. Sidewall 40 preferably tapers as shown generally toward axis 38 from lower end 30 to upper end 34. Most preferably, at least a portion of sidewall 40 is flared such that a first acute angle defined between axis 38 and sidewall 40 at lower end 30 is generally greater than a second acute angle defined between axis 38 and sidewall 40 at upper end 34. Of course, it is assumed that the interior and exterior surfaces of sidewall 40 are parallel, wherein an angle between sidewall 40 and axis 38 is considered to be the angle defined between axis 38 and a line tangent to either the exterior or interior surface of sidewall 40. Because of the cylindrical shape employed for portion 16 in the illustrated embodiment, the above defined angles will not generally be constant around the circumference of portion 18. By way of example, the difference between the above defined first acute angle and the above defined second acute angle can be about 10°. Although the precise angles employed can range widely, for the portion of sidewall 40 in the illustrated embodiment which extends upwardly from the uppermost points of portion 16 to upper end 34, the first acute angle is about 45° and the second acute angle is about 35°.

The above described shape of sidewall 40 is very effective at shielding opening 28 from ambient magnetic fields. Although the reasons for this result are not completely understood, it is speculated that the preferred shape of sidewall 40 generally conforms to the flux lines of ambient fields, especially the earth's field, and that this condition may at least partially explain the excellent shielding of opening 28. Additionally, it is presently thought that the preferred shape of sidewall 40 allows maximization of the size of opening 36 for a desired shielding effect. This factor is important since it is typically necessary that opening 36 be large enough to permit passage therethrough of hardware associated with the drill bit such as collars etc. and also large enough to allow an operator to view through opening 36 and line up a drill bit with opening 28.

Although the shape of sidewall 40 as illustrated is presently preferred, it should be understood that other shapes, such as cylindrical, are within the scope of the invention.

Figures 2, 3:
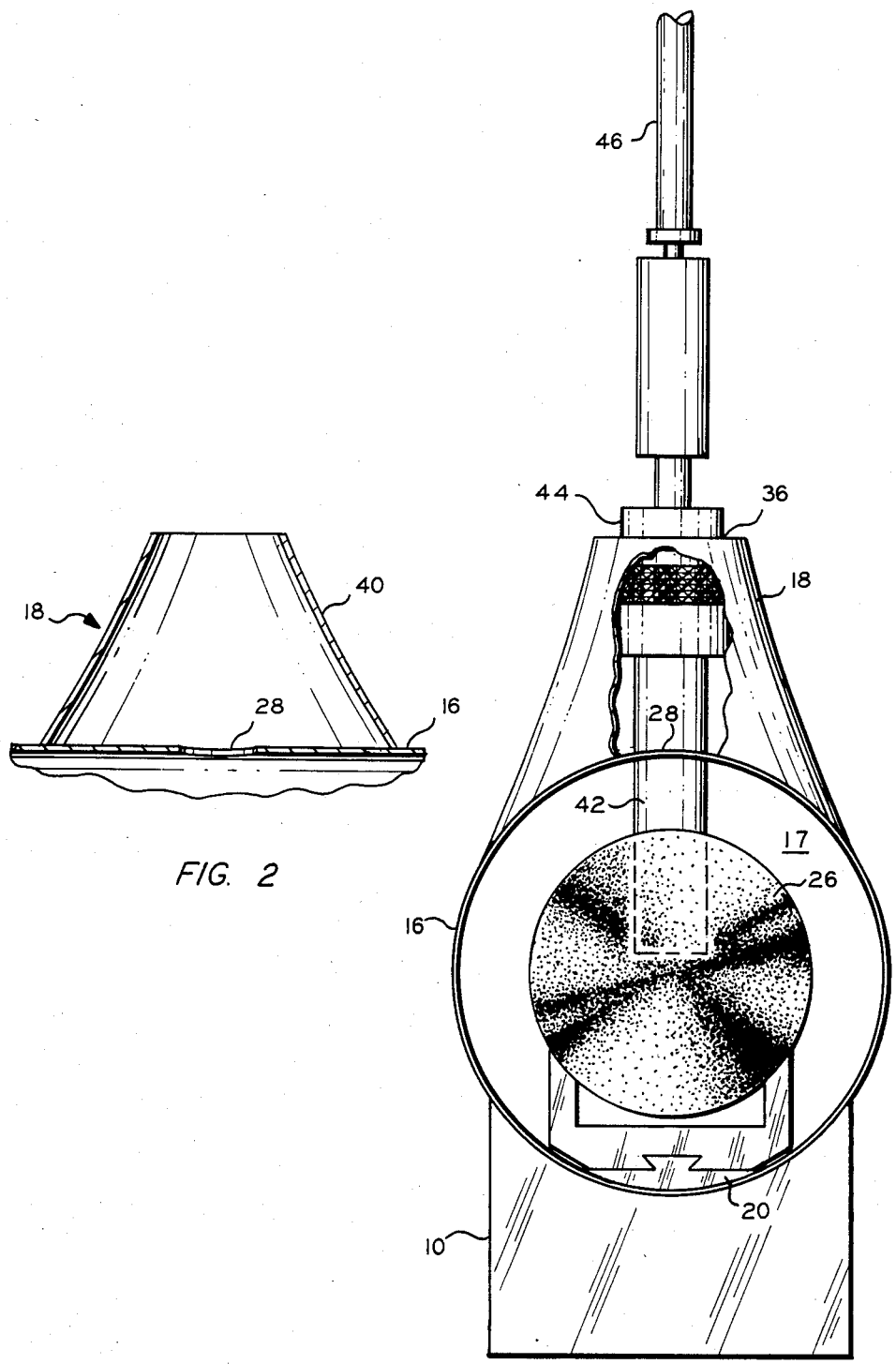
FIG. 2 is a partial longitudinal cross-sectional view of the apparatus shown in FIG. 1.
FIG. 3 is an end view of the apparatus shown in FIG. 1, wherein a portion of the apparatus is broken away. The apparatus is shown as being utilized in the drilling of a borehole core. In this regard, a drill bit is also shown in FIG. 3 in cutting contact with the borehole core.

Referring now to FIG. 2 a partial cross-sectional view of the FIG. 1 apparatus is shown. Portion 18 is illustrated as being hollow. In addition, sidewall 40 has an interior surface which defines an interior space therein which is in communication with opening 28. For optimum shielding of opening 28, it is also preferred that opening 28 be spaced inwardly from the interior surface of sidewall 40 where it meets the exterior surface of portion 16. More specifically, a boundary is defined where the interior surface of sidewall 40 meets the exterior surface of portion 16, wherein the boundary is closed, surrounds the perimeter of opening 28, and is also spaced from the opening perimeter.

Referring now to FIG. 3, an end view of the FIG. 1 apparatus is shown as being in use in a drilling operation, wherein a portion of the apparatus is broken away to show internal details discussed below.

A drill bit 42 is shown as extending through opening 28 and into chamber 17 so as to come into cutting contact with borehole core 26. Drill bit 42 is hollow so that as the bit cuts into the core, a drilled core specimen extends up into the bit. Most preferably, bit 42 is diamond tipped, and made of a nonmagnetic alloy which will not become magnetized and contribute to the ambient fields to which core 26 is exposed. A nonmagnetic bit as described above can be specially ordered from Felker Operations, Dresser Industries, Inc. of Torrance, Calif.

Drill bit 42 is operably connected at its upper end to collar 44 which is shown as extending through opening 36. Thus, in the illustrated embodiment, opening 36 is not only large enough to accomodate drill bit 42, but is also large enough to accomodate collar 44. If desired, sufficient clearance can be provided between the interior surface of portion 18 and collar 44 at opening 36 so as to allow an operator to view through opening 36 as discussed above. It should be understood that if bit 42 was of sufficient length, there would be no need to make opening 36 large enough to accomodate collar 44.

Collar 44 is operably connected through several intermediate parts to a drive shaft 46, which is only partially shown. Drive shaft 46 is operably connected at its upper end to conventional drive equipment (not shown) for rotating shaft 46 and bit 42. Drive shaft 46 is commonly constructed of a magnetic steel alloy which is usually magnetized to some extent from stress, heat etc., and thus contributes to the ambient magnetic field. Preferably, shaft 46 is constructed of a nonmagnetic alloy. A shaft of such an alloy is not generally commercially available, and would thus have to be custom made.

To further optimize the magnetic shielding of borehole core 26 during drilling, shielding member 14 and base 10 can be housed in a box (not shown) constructed of an alloy having a moderately high permeability such as an electrical steel. Preferably, such a box is demagnetized before using by exposing it to an AC magnetic field having a frequency of, for example, 60 Hz. A box constructed of an electrical steel is usually magnetized during construction from stress, heat of welding, etc., thus necessitating demagnetization.

In operation, the apparatus shown in the FIGURES operates as follows. A borehole core is secured to support member 24 by any suitable means such as by straps (not shown) of a nonmagnetic material. The support member 24 and borehole core 26 thereon are then inserted through an open end of portion 16 by moving support member 24 along track 20, the borehole core being positioned for drilling so as to be adjacent to opening 28. Typically, a mark is place on borehole core 26 before insertion into the apparatus, this mark being the desired spot for drilling. The core 26 is positioned visually by peering through openings 36 and 28, and adjusting the position of core 26 until the core mark and openings 28 and 36 are properly aligned. Proper positioning can be further aided by providing a stylus, which is essentially a vertical elongated member, on one end of base 10. A raised mark at the desired drilling spot or a mark on the end of borehole core can be aligned with opening 28 utilizing such a stylus.

Drill bit 42 is lowered by conventional means so as to be inserted through opening 36, and then through opening 28 so as to extend into chamber 17. The bit is lowered until it comes into contact with borehole core 26, and bit 42 is rotated by the drive equipment so as to cut a core specimen from the borehole core. As noted above, bit 42 is hollow, so that the drilled specimen extends up into the bit. Preferably, a fluid such as salt water, i.e. simulated formation water, is continuously circulated down through the center of the bit by means not shown in order to cool the bit and wash away cuttings. Drilling is continued until the desired core specimen is obtained. The size of the core specimen depends primarily on the magnetic analysis equipment being employed to analyze the specimen. A typical core specimen can be, for example, several inches long and about 1 inch in diameter. Once drilling is completed, the borehole core is removed from the apparatus. The core specimen is removed from the borehole core by inserting a suitable elongated object such as a screwdriver (preferably nonmagnetic) into the annular space drilled out by the bit, and then manually applying stress to the bottom of the specimen until it breaks loose.

Several examples will now be described to further illustrate the invention. These examples should not be construed to limit the invention in any manner. Certain procedures common to all of the examples, and also some background information are set forth below.

In each of the examples, borehole core samples were 4-inch diameter core samples (sometimes referred to hereinafter as simply "cores" or "borehole cores") of reservoir sandstone from the Burbank Field, Osage County, Okla. The cores were taken at between 2970 and 2980 feet. Series of large core specimens, 1 inch in diameter and 2.5 inches in length, were drilled from a borehole core in each example. For the sake of clarity, these large core specimens will be referred to as "plugs". More specifically, a series of antiparallel plug pairs were drilled for each example, each pair being spaced longitudinally from an adjacent pair. Each plug pair consists of a first plug drilled from one side of the core, and a second plug drilled from the opposite side of the core. Each of the plugs were drilled as closely adjacent to one another as possible, most typically less than about ⅛ inch apart. As used hereinafter for a particular plug pair, M denotes one plug drilled from one side of the core, and Z denotes the other plug drilled from the opposite side. After removing the plugs from the borehole core, an end piece of each plug was sawed off. This end piece, about ⅛ inch to about ½ inch long, has an end face which formed a portion of the borehole core exterior surface. Removing the end piece of a plug in this manner assists in avoiding edge effects in analysis. The remaining portion of the plug was sawed in half to yield two core specimens for analysis, hereinafter denoted as A and B, each 0.9 inch in length. All sawing was performed with a nonmangetic saw having copper blades.

Again in each of the examples, an SCT (Superconducting Technologies Division, United Scientific Corporation, Santa Clara, Calif.) cryogenic magnetometer was used to measure the direction of the magnetism in each core specimen. This analysis was performed in a magnetically shielded room or vault to avoid the temporary "soft" magnetization which can result from exposure to the earth's field. The magnetic flux density in the room was measured to be 150 gammas (1 gamma = $10^{-5}$ gauss, and the earth's field has a flux density of about 0.5 gauss). The magnetometer detects the magnetization vector for each core specimen, wherein the vector direction is expressed in terms of two angles, declination and inclination. Declination is the compass bearing of the measured direction. In other words, the declination angle is derived from the projection of the magnetizattion vector in a horizontal plane, the declination angle being measured clockwise from North. Inclination is the angle up or down from the horizontal.

The output data from the magnetometer was coupled into a digital computer for processing. The computer was programmed to invert the measured direction 180° for one of the M or Z group of specimens. After processing, then, the direction for this group of specimens is opposite to the original direction.

The effect of overprinting on the declination angle will now be discussed. As will become more apparent below, the declination angle is the angle which most clearly indicates the existence of overprinting. First, one must visualize two antiparallel specimens oriented generally horizontally as they would have been in the borehole. If no overprinting from ambient fields occurred during drilling, the magnetization vector, and thus the declination angle, would naturally be the same for each specimen, since the only magnetism in the specimen is the natural remanent magnetism. However, if overprinting occurs during drilling, the magnetization vector will be the sum of not only the NRM (natural remanent magnetism) vector, but also the overprinting vector. Moreover, the overprinting vector is parallel to the longitudinal axis of the core specimen for each of the M and Z specimens, but in opposite directions. As noted above, the overprinting vectors are in these directions because of the very steep (nearly vertical) flux lines of the earth's field and the nearly vertical flux lines from a magnetized drill bit drive shaft to which the core specimen is exposed. During drilling, the heat and stress of drilling causes the specimen to pick up a relatively "hard" magnetization accordingly. Because the overprinting vectors for antiparallel M and Z specimens are oppositely directed, their summation with their respective NRM (natural remanent magnetism) vectors causes the resultant vectors to have different directions. Thus, the projections of the resultant vectors in a horizontal plane, which can be denoted as declination vector components, also have different directions and corresponding declination angles. As overprinting increases the angle (of less than 180°) defined between the M and Z declination vector components increases for uncorrected actual vectors. As previously noted, the M and Z specimens are considered to be horizontally disposed in the above discussion.

Also as noted previously, the computer inverts one of the resultant magnetization vectors for either the M or Z specimen. Thus, for no overprinting, after the computer correction, the declination angles for M and Z specimens differ by 180°. As the degree of overprinting increases, the difference between ΔDec (the difference between the M and Z declination angles) and the ideal 180° value increases. For infinite overprinting, the difference between declination angles would be zero.

It should also be noted that inclination angles for M and Z specimens are ideally equivalent, this condition also being indicative of an absence of overprinting.

The drill bit utilized in each of the examples was a type SICD diamond tipped, nonmagnetic 1 inch I.D. drill bit, described previously, manufactured by Felker Operations, Dresser Industries, Inc. The drive shaft was composed of a nonmagnetic stainless steel alloy, and the drive equipment employed was conventional drill press equipment.

EXAMPLE I

A shielding apparatus for use in core specimen drilling was constructed, the apparatus being substantially similar to that shown in FIGS. 1-3. Portion 16 was constructed from Mumetal, described above, manufactured by Allegheny Ludlum Steel Company. The portion 18 material was Eagle AAA foil, manufactured by Eagle Magnetic Company. The foil was formed by hand so as to result in a shape substantially similar to that illustrated for portion 18. In addition, lower end 30 of portion 18 was attached to the exterior surface of portion 16 with black electrical tape. Base 10, track 20, and support member 24 were all made of aluminum. In addition to the apparatus shown in the FIGURES, the apparatus as shown in FIG. 1 was enclosed within an electrical steel (Steel-M-22, CP-3, 24 gauge, from Cook Electrical Steel of Dearborn, Mich.) box 30 inches wide, 22 inches deep, 17 inches high having a suitable large opening at its top for receiving a drill bit therethrough. The box was demagnetized by exposing it to an AC magnetic field having a frequency of 60 Hz. As noted above, such a box is not necessary, but it serves to optimize the shielding effect. Important dimensions are set forth in Table IA.

TABLE IA

| Item | Dimension |
|---|---|
| Portion 16 | |
| Thickness of wall | .030 in. |
| Length | 20 in. |
| Inside diameter | 5 in. |
| Diameter of opening 28 | 1.5 in. |
| Portion 18 | |
| Thickness of wall | .004 in. |
| Height | 4 in. |
| Maximum diameter, as measured longitudinally at lower end 30 | 7 in. |
| Acute angle* defined between sidewall 40 and axis 38 at lower end 30 | 45° |
| Acute angle* defined between sidewall 40 and axis 38 at upper end 34 | 35° |
| Diameter of opening 36 | 2.75 in. |

*These angles are measured for the portion of sidewall 40 which extends upwardly from the uppermost points of portion 16 to upper end 34.

The flux density for the vertical field component was measured to be 35 gammas at a position ¼ inch below opening 28.

A borehole core section was drilled as described above and in a fashion substantially similar to that illustrated in FIG. 3. Four antiparallel plug pairs were drilled, thus yielding four M plugs and four antiparallel Z plugs. The M and Z plugs were removed from the borehole core and sawed in half to give A and B specimens corresponding to each plug. Thus, 16 specimens were obtained. Moreover, each plug pair was drilled such that adequate space existed between each pair to allow for subsequent drilling of additional plug pairs in these spaces according to Example II. The magnetism directions for each specimen was measured. The declination and inclination angles thus obtained for each specimen are given in Table IB.

TABLE IB

| Specimen | Declination (degrees) | Inclination (degrees) |
|---|---|---|
| M-1A | 299.5 | 56.6 |
| M-1B | 295.8 | 64.7 |
| M-2A | 309.5 | 64.2 |
| M-2B | 304.3 | 65.8 |
| M-3A | 297.6 | 58.1 |
| M-3B | 329.9 | 71.0 |
| M-4A | 348.3 | 63.8 |
| M-4B | 345.8 | 69.4 |
| Z-1A | 119.4 | 70.7 |
| Z-1B | 149.6 | 68.0 |
| Z-2A | 131.4 | 63.2 |
| Z-2B | 115.8 | 68.9 |
| Z-3A | 131.6 | 58.9 |
| Z-3B | 113.3 | 60.9 |
| Z-4A | 120.9 | 65.9 |
| Z-4B | 119.2 | 70.1 |

The vector mean was calculated for the magnetic vector directions for each (M and Z) group of specimens to give a corresponding mean declination ($\overline{Dec}$) angle and a mean inclination ($\overline{Inc}$) angle. Standard Fisher statistics were utilized to obtain the mean values. Reference is made to Methods in Paleomagnetism ed. by Collinson, Creer and Runcorn, Elsevier Publishing Company, pages 313-321 for a discussion of such statistical techniques. Table IC sets forth mean declination and inclination angles and their corresponding $a_{95}$ values. $a_{95}$ is the angle of the cone of confidence, and is essentially an error limit value. Discussion of $a_{95}$ can also be found in Collinson et al.

TABLE IC

| Specimen Group | $\overline{Dec}$ | $\overline{Inc}$ | $a_{95}$ |
|---|---|---|---|
| M | 313.99 | 65.57 | 7.16 |
| Z | 125.24 | 66.22 | 4.44 |

The difference between the mean declination angles for the M and Z groups, herein denoted as $\Delta\overline{Dec}$, is about 189°. $\Delta\overline{Inc}$ is approximately zero.

The $\Delta\overline{Dec}$ value of 189° is very close to the 180° case for no overprinting. Moreover, a portion of the 9° deviation from the ideal 180° value could be attributed to statistical error. The $\Delta\overline{Inc}$ value of approximately zero is also evidence of the absence of overprinting.

Thus, the above data shows that very little magnetic overprinting from ambient fields occurred during drilling with the preferred shielding apparatus.

EXAMPLE II

This example is essentially a control example wherein no magnetic shielding was utilized during drilling. The vertical component of the ambient earth's field without any shielding was measured to be 25,600 gammas.

Three antiparallel plug pairs were drilled from the same borehole core section utilized in Example I. The borehole core was contained in a nonmagnetic aluminum box during drilling. This box was used solely to receive drilling fluid. Each plug pair was drilled in a space between the areas from which plugs were removed in Example I. Each plug was sawed in half to result in A and B specimens which were then analyzed. Given in Table IIA are results of this analysis.

TABLE IIA

| Specimen | Declination (degrees) | Inclination (degrees) |
|---|---|---|
| M-5A | 309.07 | 67.48 |
| M-5B | 309.99 | 68.91 |
| M-6A | 305.26 | 66.42 |
| M-6B | 320.25 | 65.49 |
| M-7A | 281.47 | 75.75 |
| M-7B | 313.80 | 76.32 |
| Z-5A | 136.13 | 70.53 |
| Z-5B | 134.79 | 71.05 |
| Z-6A | 143.81 | 73.93 |
| Z-6B | 118.37 | 76.48 |
| Z-7A | 182.47 | 76.72 |
| Z-7B | 169.76 | 82.18 |

A vector mean was taken as in Example I. Mean values and $a_{95}$ values are given in Table IIB.

TABLE IIB

| Specimen Group | $\overline{Dec}$ | $\overline{Inc}$ | $a_{95}$ |
|---|---|---|---|
| M | 308.07 | 70.40 | 5.20 |
| Z | 144.09 | 76.02 | 5.83 |

$\Delta\overline{Dec}$ is calculated to be about 164°. This value is significantly less, 16°, than the value of 180° which corresponds to the absence of overprinting. As noted above, as overprinting increases, the difference between $\Delta\overline{Dec}$ and 180° should also increase. Furthermore, $\Delta\overline{Inc}$ is calculated as about 6°. Thus, drilling without shielding according to present example resulted in significant overprinting.

EXAMPLE III

Four antiparallel plug pairs were drilled from another section of borehole core utilizing the same shielding apparatus as described in Example I. Thus, 16 specimens were obtained. A slightly different drilling procedure was used in this example, in that the plugs drilled with the complete shielding apparatus were not removed from the borehole core before plugs were drilled according to Example IV (discussed below, drilling being performed without portion 18 of the shielding apparatus). Spaces were left between plug pairs for the drilling of plugs in Example IV in a manner similar to that discussed in Example I.

Declination and inclination data for specimens drilled according to this example are shown in Table IIIA.

TABLE IIIA

| Specimen | Declination (degrees) | Inclination (degrees) |
| --- | --- | --- |
| M-8A | 296.4 | 74.5 |
| M-8B | 304.8 | 65.0 |
| M-9A | 280.9 | 79.3 |
| M-9B | 317.8 | 68.5 |
| M-10A | 307.2 | 69.1 |
| M-10B | 325.1 | 64.8 |
| M-11A | 9.7 | 82.6 |
| M-11B | 326.2 | 73.7 |
| Z-8A | 154.0 | 77.3 |
| Z-8B | 128.5 | 84.0 |
| Z-9A | 137.1 | 71.0 |
| Z-9B | 79.9 | 79.5 |
| Z-10A | 110.6 | 72.1 |
| Z-10B | 95.5 | 72.0 |
| Z-11A | 229.5 | 84.5 |
| Z-11B | 187.7 | 87.3 |

Mean values and $\alpha_{95}$ values are given in Table IIIB.

TABLE IIIB

| Specimen Group | $\overline{Dec}$ | $\overline{Inc}$ | $\alpha_{95}$ |
| --- | --- | --- | --- |
| M | 313.50 | 73.02 | 6.01 |
| Z | 123.17 | 80.47 | 6.50 |

Thus, $\Delta\overline{Dec}$ is 190.33. This result compares favorably with the result obtained in Example I, and is evidence of very little overprinting. $\Delta\overline{Inc}$ is calculated to be about 7.5.

EXAMPLE IV

Four plug pairs were drilled from the section of borehole core employed in Example III. As noted above, these plugs were drilled before the plugs of Example III were removed from the borehole core. Drilling was performed without portion 18 of the shielding apparatus in place. The flux density for the vertical field component was measured to be 460 gammas at a position ¼ inch below opening 28 without portion 18 in place.

Declination and inclination data are given in Table IVA.

TABLE IVA

| Specimen | Declination (degrees) | Inclination (degrees) |
| --- | --- | --- |
| M-12A | 302.6 | 68.9 |
| M-12B | 312.2 | 73.4 |
| M-13A | 341.5 | 72.0 |
| M-13B | 349.5 | 71.9 |
| M-14A | 314.7 | 67.2 |
| M-14B | 317.8 | 66.8 |
| M-15A | 4.8 | 80.9 |
| M-15B | 16.4 | 82.2 |
| Z-12A | 144.6 | 80.3 |
| Z-12B | 53.8 | 85.0 |
| Z-13A | 144.5 | 74.8 |
| Z-13B | 70.2 | 81.4 |
| Z-14A | 105.0 | 80.7 |
| Z-14B | 291.7 | 85.3 |
| Z-15A | 95.0 | 73.3 |
| Z-15B | 104.8 | 72.0 |

Table IVB sets forth mean declination and inclination values and $\alpha_{95}$ values based on the data in Table IVA.

TABLE IVB

| Specimen Group | $\overline{Dec}$ | $\overline{Inc}$ | $\alpha_{95}$ |
| --- | --- | --- | --- |
| M | 327.77 | 74.08 | 6.12 |
| Z | 107.92 | 81.40 | 6.07 |

$\Delta\overline{Dec}$ is equal to 220°, 40° from the 180° ideal core for no overprinting. Compare this 40° discrepancy, with portion 18 removed, with the relatively small 10° discrepancy in Example III, wherein the complete shielding apparatus is employed. It can be seen from this comparison that the presence of portion 18 makes a significant contribution to the shielding of opening 28, and thus of the core being drilled.

It might be noted that the above noted 40° discrepancy is greater than that discrepancy, 16°, obtained in Example II where no shielding was employed. This result on its face is rather incongruous. However, it should be noted that different borehole core sections were employed in each of Examples II and IV. It is speculated that these different core sections were significantly different in magnetic properties due to, for example, different concentrations of magnetite. The magnetic behavior of the two core sections would be expected to differ also.

Thus, there is provided by the present invention an apparatus and method wherein a borehole core is effectively shielded from ambient magnetic fields. Little or no magnetic overprinting from ambient fields results in a core specimen drilled according to the invention. Therefore, it is not necessary to drill two antiparallel specimens to cancel out overprinting as in the above described prior method, thereby resulting in significant savings in both cost and time.

Obviously many modifications and variations of the present invention are possible in light of the above teachings. It is therefore to be understood that within the scope of the appended claims the invention may be practiced otherwise than as specifically described.

What is claimed is:

1. A magnetic shielding member comprising:
   a first hollow portion which includes a wall having a first opening therethrough, said wall having an exterior surface, wherein said first portion is composed of a ferromagnetic material characterized by an initial magnetic permeability of at least about 10,000 gauss/oersted; and
   a second hollow portion, having an axis, of a ferromagnetic material also characterized by an initial permeability of at least about 10,000 gauss/oersted, wherein said second portion has a first end at which said second portion meets said first portion at said exterior surface, said second portion also having a second open end generally opposite said first end and a sidewall which extends between said ends and which extends outwardly from said exterior surface so as to generally surround said first opening and so as to generally taper toward said axis from said first end to said second open end, at least a portion of said second portion sidewall being flared such that a first acute angle defined between said axis and said sidewall near said first end is greater than a second acute angle defined between said axis and said sidewall near said second end, the difference between the first acute angle and the second acute angle being about 10°, and wherein said sidewall has an interior surface which defines an interior space therein which communicates with said first opening.

2. A shielding member as recited in claim 1, wherein a boundary is defined where said sidewall interior surface meets said exterior surface of said first portion wall, said boundary being generally closed and surrounding the perimeter of said first opening, and wherein said boundary is spaced from said perimeter.

3. A shielding member as recited in claim 1, wherein the first acute angle is about 45° and the second acute angle is about 35° for at least a portion of the flared sidewall.

4. A shielding member as recited in claim 2 wherein said first portion has a longitudinal axis, said second portion axis being generally perpendicular to said first portion longitudinal axis.

5. A shielding member as recited in claim 4, wherein said second open end defines a second opening, and wherein said second portion axis intersects the centers of said first and second openings.

6. A shielding member as recited in claim 5, wherein said first portion is generally cylindrical in shape.

7. A shielding member as recited in claim 6, wherein said cylindrical first portion has two open ends.

8. A shielding member as recited in claim 7, wherein said first opening is located at approximately the longitudinal center of said cylindrical first portion.

9. A shielding member as recited in claim 8, wherein said first and second portions are separate members, wherein said first portion is mounted to said second portion such that said second portion is in intimate contact, at said first end, with the exterior surface of said first portion wall.

10. A shielding member as recited in claim 1, wherein the first portion material and the second portion material are characterized by an initial permeability of at least 20,000 gauss/oersted.

11. A shielding member as recited in claim 10, wherein the first portion material and the second portion material are characterized by a coercivity of less than about 0.1 oersted.

12. A shielding member as recited in claim 11, wherein the ferromagnetic material for each of said portions is a metallic alloy selected from the group consisting of 4–79 Permalloy, Supermalloy, Mumetal, 1040 alloy, and Sendust.

13. An apparatus comprising:
a shielding member which includes a first hollow portion composed of a ferromagnetic material characterized by an initial magnetic permeability of at least about 10,000 gauss/oersted, said first portion having an interior surface which defines a chamber therein, wherein said first portion includes a wall having a first opening therethrough in communication with the said chamber; and
a drilling means, said drilling means including a drill bit adapted to be received through said first opening so as to extend into said chamber.

14. An apparatus as recited in claim 13, wherein said shield member further includes a second hollow portion of a ferromagnetic material also characterized by an initial magnetic permeability of at least about 10,000 gauss/oersted, said second portion having a first end at which said second portion meets said first portion at said exterior surface, said second portion also having a second open end generally opposite said first end and a sidewall which extends between said ends, wherein said side wall extends outwardly from said exterior surface so as to generally surround said first opening, and wherein said sidewall has an interior surface which defines an interior space therein, said interior space being in communication with said first opening, and wherein said second open end defines a second opening which is also adapted to receive said drill bit therethrough, said first and second openings being aligned with each other.

15. An apparatus as recited in claim 14 wherein said second portion has an axis, and wherein said sidewall generally tapers toward said axis from said first end to said second open end.

16. An apparatus as recited in claim 15, wherein a boundary is defined where said sidewall interior surface meets the exterior surface of said first portion wall, said boundary being generally closed and surrounding the perimeter of said first opening, said boundary being spaced from said perimeter.

17. An apparatus as recited in claim 16, wherein at least a portion of said second portion sidewall is flared such that a first acute angle defined between said axis and said sidewall at said first end is greater than a second acute angle defined between said axis and said sidewall at said second end.

18. An apparatus as recited in claim 13, wherein said first portion is generally cylindrical in shape.

19. An apparatus as recited in claim 18, further comprising: a base composed of a nonmagnetic material, said first cylindrical portion being fixedly mounted to said base; a track composed of a nonmagnetic material fixedly mounted to said first cylindrical portion and said base so as to extend through said chamber within said first cylindrical portion and so as to be in direct contact with the interior surface of said first cylindrical portion; and a sliding support member, also of a nonmagnetic material, slidably mounted to said track, said support member being adapted to support a borehole core thereon for drilling.

20. An apparatus as recited in claim 19, wherein said drill bit is constructed of a nonmagnetic alloy.

21. An apparatus as recited in claim 13, wherein the ferromagnetic material for each of said portion is a metallic alloy selected from the group consisting of 4–79 Permalloy, Supermalloy, Mumetal, 1040 alloy, and Sendust.

22. A method of drilling a core specimen from a borehole core comprising:
positioning the borehole core in a chamber defined within a hollow shielding member which has at least one opening in a wall thereof, said member being composed of a ferromagnetic material, wherein the borehole core is positioned adjacent to the opening;
drilling a core specimen from the borehole core with a drilling means which includes a drill bit, wherein the drill bit is inserted through the opening so as to extend into the chamber and come into cutting contact with the borehole core.

23. A method as recited in claim 22, wherein the ferromagnetic material is characterized by an initial magnetic permeability of at least about 10,000 gauss/oersted.

24. A method as recited in claim 23, wherein the ferromagnetic material is a metallic alloy selected from the group consisting of 4–79 Permalloy, Supermalloy, Mumetal, 1040 alloy and Sendust.

25. A method as recited in claim 22, wherein said positioning step includes inserting the borehole core through an open end of the hollow member, the member being generally cylindrical.

26. A method as recited in claim 25, wherein said hollow member has a track mounted therein, and a support member slidably mounted on the track, said borehole core being supported on said support member, wherein said borehole core is positioned within said chamber by moving said support member, and thus the borehole core thereon, along said track.

27. A method as recited in claim 26, wherein said shielding member includes a first portion having said chamber defined therein and having a first opening through a wall thereof, said shielding member also including a second portion having a side wall which extends outwardly from the exterior surface of said first portion to a second portion open end which defines a second opening, wherein in said drilling step said drill bit is extended through said first opening and said second opening so as to extend into said chamber.

* * * * *